US012559469B2

(12) United States Patent
Li et al.

(10) Patent No.: US 12,559,469 B2
(45) Date of Patent: Feb. 24, 2026

(54) CYCLIC THIOETHER COMPOUND, VEGETABLE OIL COMPOSITION CONTAINING THE SAME, THEIR PREPARATION AND APPLICATION THEREOF

(71) Applicants: CHINA PETROLEUM & CHEMICAL CORPORATION, Beijing (CN); SINOPEC OILFIELD SERVICE CORPORATION, Beijing (CN); SINOPEC SHENGLI PETROLEUM ENGINEERING CO., LTD, Shandong (CN); DRILLING TECHNOLOGY RESEARCH INSTITUTE OF SINOPEC SHENGLI PETROLEUM ENGINEERING CO., LTD, Shandong (CN)

(72) Inventors: Gongrang Li, Shandong (CN); Wenbo Li, Beijing (CN); Chengjun Wang, Shandong (CN); Bingxiang Sun, Beijing (CN); Hui Tian, Shandong (CN); Ke Li, Shandong (CN); Jianghong Jia, Shandong (CN); Xudong Wang, Shandong (CN); Lei Yu, Shandong (CN); Jun Wang, Shandong (CN); Wei Wang, Shandong (CN); Lei Li, Shandong (CN)

(73) Assignees: CHINA PETROLEUM & CHEMICAL CORPORATION, Beijing (CN); SINOPEC OILFIELD SERVICE CORPORATION, Beijing (CN); SINOPEC SHENGLI PETROLEUM ENGINEERING CO., LTD, Shandong (CN); DRILLING TECHNOLOGY RESEARCH INSTITUTE OF SINOPEC SHENGLI PETROLEUM ENGINEERING CO., LTD, Shandong (CN)

( * ) Notice: Subject to any disclaimer, the term of this patent is extended or adjusted under 35 U.S.C. 154(b) by 421 days.

(21) Appl. No.: 17/904,726

(22) PCT Filed: Jan. 28, 2021

(86) PCT No.: PCT/CN2021/074118
§ 371 (c)(1),
(2) Date: Aug. 22, 2022

(87) PCT Pub. No.: WO2022/160171
PCT Pub. Date: Aug. 4, 2022

(65) Prior Publication Data

US 2023/0141112 A1 May 11, 2023

(51) Int. Cl.
*C07D 331/04* (2006.01)
*C07D 277/74* (2006.01)
*C09K 8/035* (2006.01)

(52) U.S. Cl.
CPC ......... *C07D 331/04* (2013.01); *C07D 277/74* (2013.01); *C09K 8/035* (2013.01)

(58) Field of Classification Search
None
See application file for complete search history.

(56) References Cited

U.S. PATENT DOCUMENTS

| | | | |
|---|---|---|---|
| 2,695,286 A | 11/1954 | Dearborn | |
| 2,729,634 A | 1/1956 | Dearborn | |
| 2,845,438 A | 7/1958 | Dearborn | |
| 3,849,454 A | 11/1974 | Magne et al. | |
| 3,873,457 A | 3/1975 | Magne et al. | |

FOREIGN PATENT DOCUMENTS

| | | | | |
|---|---|---|---|---|
| CN | 100519687 C | 7/2009 | | |
| CN | 103254168 A | * | 8/2013 | ........... C07D 331/02 |
| CN | 103571441 A | 2/2014 | | |
| CN | 103937468 A | 7/2014 | | |
| CN | 107098917 A | 8/2017 | | |
| DE | 947364 C | 8/1956 | | |

(Continued)

OTHER PUBLICATIONS

PubChem CID 101972309, National Center for Biotechnology Information. PubChem Compound Summary for CID 101972309, Methyl 2-(3-undecylthiiran-2-yl)acetate. https://pubchem.ncbi.nlm.nih.gov/compound/Methyl-2-_3-undecylthiiran-2-yl_acetate. Accessed Apr. 15, 2025, create date Dec. 19, 2015. (Year: 2015).*
Chemical Abstract Registry No. 58401-52-8, indexed in the Registry file on STN CAS ONLINE Nov. 16, 1984. (Year: 1984).*
Chemical Abstract Registry No. 58401-53-9, indexed in the Registry file on STN CAS ONLINE Nov. 16, 1984. (Year: 1984).*
Chemical Abstract Registry No. 32519-44-1, indexed in the Registry file on STN CAS ONLINE Nov. 16, 1984. (Year: 1984).*
Chemical Abstracts Registry No. 114000-49-6, indexed in the Registry file on STN CAS ONLINE Apr. 23, 1988. (Year: 1988).*
A machine generated English translation of CN 103254168 A (Wang et al.). (Year: 2013).*

(Continued)

*Primary Examiner* — Laura L Stockton
(74) *Attorney, Agent, or Firm* — NKL Law; Allen Xue

(57) ABSTRACT

A cyclic thioether compound has a structure represented by the following formula (I). A vegetable oil composition contains the cyclic thioether compound. When the cyclic thioether compound is used as a drilling fluid lubricant in a drilling fluid. The lubrication performance of the drilling fluid can be significantly improved.

(I)

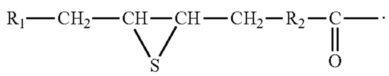

8 Claims, 2 Drawing Sheets

(56) References Cited

FOREIGN PATENT DOCUMENTS

WO 2017167989 A1 10/2017

OTHER PUBLICATIONS

Falck J. R. et al., "11, 12-epoxyeicosatrienoic acid (11,12-EET): structural determinants for inhibition of TNF-alpha- induced VCAM-1 expression", Bioorganic & Medicinal Chemistry Letters, Nov. 17, 2003, vol. 13, No. 22, pp. 4011-4014.
PubChem CID 23466394, National Center for Biotechnology Information, PubChem Compound Summary for CID 23466394, N, N-dibutyl-9, 10-epithiostearamide. https://pubchem.ncbi.nlm.nih.gov/compound/N_N-dibutyl-9_10-epithiostearamide. Accessed Apr. 15, 2025, create date Dec. 12, 2007. (Year: 2007).
Marcel, S.F. et al.; "Synthesis and physical properties of some 2, 3- and 2, 2-epithio C18 fatty acid derivatives", Chemistry and Physics of lipids; vol. 49, No. 3, Dec. 31, 1988; pp. 167-178.
Wright, Stephen W. et al.; "Episulfide Inhibitors of Lipoxygenase"; Bioorganic & Medicinal Chemistry Letters; vol. 2, No. 11, Dec. 31, 1992; pp. 1385-1390.
Magne, F.C. et al.; "Lubricants and lubricant additives: II. Performance characteristics of some substituted fatty acid esters"; Journal of the American Oil Chemists' Society; vol. 52, No. 12; Dec. 31, 1975; pp. 494-497.
Dittmer, Donald C. et al.; "Derivatives of Thiacyclobutene (Thiete) and Thiacyclobutane (Thietane). I.1-3 Reactions of Thiete Sulfone"; Journal of the American Chemical Society; vol. 84, Feb. 5, 1962; pp. 399-402.
Kaufmann, H. P. et al.; "Epoxy and episulfide compounds in the field of fats.II. The literature of episulfides and the preparation of episulfides from epoxides"; Fette. Seifen. Anstrichmittel; vol. 65; Dec. 31, 1963; pp. 625-633.
Roomi, Mohammad Wadeeduddin et al.; "Stereochemical Relationships between Epithio, Halomercapto and Hydroxymercapto Derivatives of Oleic and Elaidic Acids"; Fette. Seifen. Anstrichmittel; vol. 69, No. 10; Dec. 31, 1967; pp. 778-780.

* cited by examiner

CYCLIC THIOETHER COMPOUND, VEGETABLE OIL COMPOSITION CONTAINING THE SAME, THEIR PREPARATION AND APPLICATION THEREOF

TECHNICAL FIELD

The present application relates to the technical field of drilling fluid. More particularly, the present application relates to a cyclic thioether compound, a vegetable oil composition containing the same, methods for their production and their application in drilling fluid compositions.

BACKGROUND ART

Along with the development of oil exploration, the drilling depth is constantly increased, the number of complex wells such as deep wells, ultra-deep wells, highly deviated wells, directional wells and horizontal wells is continuously growing, the friction torque in the drilling process is increasing, drilling sticking accidents occur frequently, the back pressure problem is serious, and the lubrication performance of the drilling fluid is urgently required to be improved. By adding a lubricant, the friction in the drilling process can be effectively reduced, and the lubrication performance of the drilling fluid can be improved.

At present, since vegetable oils are abundant in sources, environmentally friendly and biodegradable, they are widely used as starting materials for the development of drilling fluid lubricants. However, when vegetable oils are used as base oils or as lubricants, per se, they show a general lubrication effect and poor sustainability of lubricity, and are susceptible to decomposition at high temperatures. Therefore, the first step of applying vegetable oils in drilling fluid lubricants is to modify their structure, thereby improving their thermal stability and extreme pressure anti-wear performance. Among various vegetable oil modification approaches, there is an approach comprising sulfurizing a double bond of a vegetable oil with sulfur to form sulfurized vegetable oils, which approach can introduce a thioether group with an extreme pressure lubrication function into the structure of the vegetable oil to improve the extreme pressure lubrication performance of the vegetable oil, and researches indicate that the sulfurization of the double bond of the vegetable oil can effectively prevent the double bond from being oxidized and broken by bacteria, so that the oxidation resistance and stability of the vegetable oil can be improved. Now, sulfurized vegetable oils have been widely used as base oils for various drilling fluid lubricants and exhibit excellent lubrication performance.

Chinese patent No. 200710158398.1 discloses a high temperature resistant lubricant for drilling fluid prepared from animal and vegetable oil. The main starting materials of the lubricant comprise 50-70 parts of waste grease, 1-3 parts of sulfur, 3-10 parts of ethanolamine, 5-20 parts of diethylene glycol, 2-5 parts of an oil-soluble resin and 10-30 parts of graphite powder. The patent involves a sulfurization reaction of the grease derivative with sulfur, which is completed by mixing and reacting at 140-160° C. for 3-6 h.

Chinese patent No. 201310471487.7 discloses an anti-wear drag reducer for drilling fluid and preparation thereof. The main starting materials of the lubricant comprise 7-13% of vegetable oleic acid, 26-31% of cottonseed oil, 6-11% of sulfur powder, 3-5% of diethanolamine, 27-29% of kerosene, and 12-17% of auxiliary materials and other materials in total. The patent involves a sulfurization reaction of the cottonseed oil or the vegetable oleic acid with sulfur, which is completed by reacting at 160° C. for 160-230 min.

Chinese patent No. 201410178776.2 discloses a novel drilling fluid lubricant and preparation thereof. The main starting materials of the lubricant comprise 100 parts of rape oil or cotton oil and 4-20 parts of sulfur. The patent involves a sulfurization reaction of the vegetable oil or the cotton oil with sulfur, which is completed by two gradient reactions conducted at 120° C. and 150° C., respectively, and the reaction at 150° C. is conducted for 2 hours.

Although sulfurized vegetable oil gradually becomes a main starting material for research and development of drilling fluid lubricants, in the vegetable oil sulfurization reaction disclosed in the prior art, sulfur and vegetable oil are normally mixed and heated at a temperature of 150° C. or higher for no less than 2 hours. In vegetable oil sulfurization processes, the sulfurized vegetable oil formed by sulfurization at a high temperature for a long period is a black and thick material with pungent odor, while the sulfurized vegetable oil formed by sulfurization at a low temperature for a short period is insufficiently sulfurized, and shows poor lubrication effect. How to solve such a contradiction is a problem to be solved urgently in the development of sulfurized vegetable oil and even the research of drilling fluid lubricants at present.

SUMMARY OF THE INVENTION

The inventors of the present application believe that there is still a need in the art for an active sulfurization system suitable for the sulfurization of vegetable oils to improve the extreme pressure lubrication performance and thermal stability of the vegetable oils, thereby significantly improving the primary performances of existing lubricants for drilling fluids. The present application has been completed based on this knowledge.

Particularly, the present application relates to subject matters of the following aspects.

1. A cyclic thioether compound, having a structure represented by the following formula (I):

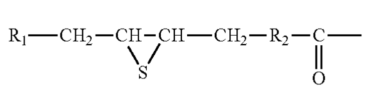

(I)

wherein in the formula (I), $R_1$ is selected from optionally substituted C1-20, C2-10, C4-8 or C6-7 linear or branched hydrocarbyl groups (such as optionally substituted C1-20, C2-10, C4-8 or C6-7 linear or branched alkyl groups, optionally substituted C2-20, C2-10, C4-8 or C6-7 linear or branched alkenyl groups, or optionally substituted C2-20, C2-10, C4-8 or C6-7 linear or branched alkynyl groups), $R_2$ is selected from single bond and optionally substituted C1-20, C2-10, C4-8 or C6-7 linear or branched hydrocarbylene groups (such as optionally substituted C1-20, C2-10, C4-8 or C6-7 linear or branched alkylene groups, optionally substituted C2-20, C2-10, C4-8 or C6-7 linear or branched alkenylene groups, or optionally substituted C2-20, C2-10, C4-8 or C6-7 linear or branched alkynylene groups), and the sum of the numbers of carbon atoms of $R_1$ and $R_2$ is 3 or more (preferably 3-35, more preferably 5-25 or 11-13).

2. The cyclic thioether compound described in any one of the preceding or subsequent aspects, having a structure represented by the following formula (I-1):

(I-1)

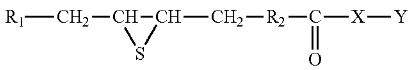

wherein in the formula (I-1), X represents O or NR', R' is selected from hydrogen and optionally substituted C1-10 linear or branched alkyl groups (preferably from hydrogen and optionally substituted C1-6 or C2-4 linear or branched alkyl groups), Y represents a monovalent end group (preferably selected from hydrogen, and optionally interrupted and optionally substituted C1-10000 linear or branched alkyl groups, more preferably from hydrogen, and optionally interrupted and optionally substituted C1-6 or C2-4 linear or branched alkyl groups, or Y represents a polyether group having a polymerization degree of between 1 and 5000 (preferably between 1 and 500)).

3. The cyclic thioether compound described in any one of the preceding or subsequent aspects, having a structure represented by the following formula (I-2):

(I-2)

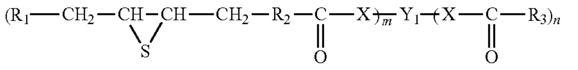

wherein in the formula (I-2), each $R_3$, being the same or different from each other, is independently selected from optionally substituted C1-39, C9-23, C11-21 or C15-19 linear or branched hydrocarbyl group (such as optionally substituted C1-39, C9-23, C11-21 or C15-19 linear or branched alkyl groups, optionally substituted C3-39, C9-23, C11-21 or C15-19 linear or branched alkenyl groups, or optionally substituted C3-39, C9-23, C11-21 or C15-19 linear or branched alkynyl groups), m is an integer of 1 or more (preferably 1, 2, 3, 4, 5 or 6), n is an integer of 0 or more (preferably 0, 1, 2, 3, 4 or 5), and m+n is an integer of 1 to 10 or 1 to 6 (such as 1, 2, 3, 4, 5 or 6), each X, being the same or different from each other, is independently selected from 0 and NR', R' is selected from hydrogen and optionally substituted C1-10 linear or branched alkyl groups (preferably from hydrogen and optionally substituted C1-6 or C2-4 linear or branched alkyl groups), $Y_1$ represents an optionally interrupted and optionally substituted m+n valent C2-10000 linear or branched alkyl group (preferably an optionally interrupted and optionally substituted m+n valent C2-6 or C2-4 linear or branched alkyl group, more preferably a 1,2,3-trivalent propyl group, or $Y_1$ represents an m+n valent polyether group having a polymerization degree of between 1 and 5000 (preferably between 1 and 500).

4. The cyclic thioether compound as described in any one of the preceeding or subsequent aspects, wherein the compound is at least one selected from the group consisting of compounds represented by the following formulae and isomers thereof:

(I-3)

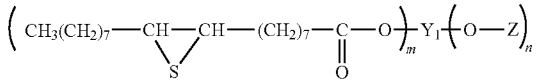

-continued (I-3-1)

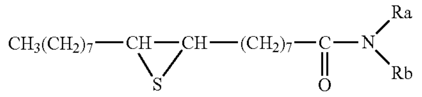

(I-3')

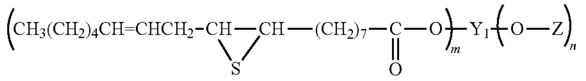

(I-3'-1)

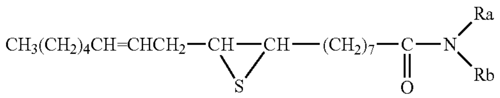

(I-3'')

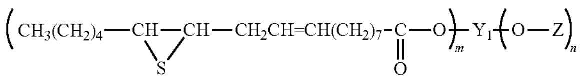

(I-3''-1)

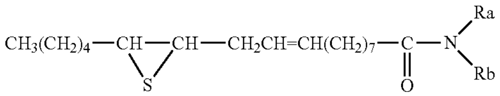

wherein in these formulae, m is an integer of 1 or more (preferably 1, 2, 3, 4, 5 or 6), n is an integer of 0 or more (preferably 0, 1, 2, 3, 4 or 5), and m+n is an integer of 1 to 10 or 1 to 6 (such as 1, 2, 3, 4, 5 or 6), and when m+n=3, $Y_1$ is a 1,2,3-trivalent propyl group, or when m=1 and n=0, $Y_1$ is an optionally interrupted and optionally substituted C2-10000 (preferably C2-6 or C2-4) linear or branched alkyl group or a polyether group having a polymerization degree of between 1 and 5000 (preferably between 1 and 500), each Z, being the same or different from each other, is independently selected from hydrogen, oleoyl group, linoleoyl group and stearoyl group, Ra and Rb, being the same or different from each other, are each independently selected from hydrogen and hydroxyl substituted C1-10 linear or branched alkyl groups (preferably from hydrogen and hydroxyl substituted C1-6 or C2-4 linear or branched alkyl groups, more preferably from hydrogen and hydroxyethyl group).

5. A method for producing a cyclic thioether compound, comprising the steps of:

subjecting an unsaturated fatty acid starting material to a sulfurization reaction in the presence of sulfur (such as elemental sulfur), a benzothiazole-based sulfurization accelerator, an inorganic zinc compound and optionally a long-chain fatty acid, to convert at least one carbon-carbon double bond of the unsaturated fatty acid starting material to a cyclic thioether moiety to obtain the cyclic thioether compound or a product mixture comprising the cyclic thioether compound, wherein the at least one carbon-carbon double bond is non-conjugated double bond.

6. The method described in any one of the preceding or subsequent aspects, wherein the unsaturated fatty acid starting material is at least one selected from the group consisting of optionally substituted C8-40 (preferably C10-24, C16-20 or C18) unsaturated fatty acid (hereinafter referred to as "unsaturated fatty acid" for short), derivatives of the unsaturated fatty acid (hereinafter, the unsaturated fatty acid and the derivative of the unsaturated fatty acid are collectively referred to as "unsaturated fatty acid compound"), and biomass materials (preferably vegetable oils) comprising the unsaturated fatty acid compound, preferably at least one selected from the group consisting of derivatives of the unsaturated fatty acid and vegetable oils comprising a derivative of the unsaturated fatty acid, and/or the vegetable oil is at least one selected from the group consisting of soybean oil, peanut oil, rapeseed oil, *camellia* seed oil and corn oil.

7. The method according to any one of the preceding or subsequent aspects, wherein the weight ratio of the sulfur: the benzothiazole-based sulfurization accelerator: the inorganic zinc compound: the unsaturated fatty acid compound (particularly the derivative of the unsaturated fatty acid): the long-chain fatty acid is 0.5-12:0.5-16:0.1-8: 60-98:0-12, preferably 1-10:0.5-5:0.1-5: 75-98:0-10 or 1-6:0.7-7.8:0.3-1.2:79-95.6:2.4-6, and/or, the weight ratio of the sulfur:the benzothiazole-based sulfurization accelerator: the inorganic zinc compound: the biomass material (particularly the vegetable oil): the long-chain fatty acid is 0.5-12:0.5-16:0.1-8: 60-98:0-12, preferably 1-10:0.5-5:0.1-5: 75-98:0-10 or 1-6: 0.7-7.8:0.3-1.2:79-95.6:2.4-6.

8. The method according to any one of the preceding or subsequent aspects, wherein the derivative of the unsaturated fatty acid is at least one selected from the group consisting of anhydride of the unsaturated fatty acid, amide of the unsaturated fatty acid (such as monoamide, diamide, triamide and the like produced from the unsaturated fatty acid and a compound having one or more primary and/or secondary amino groups per molecule) and ester of the unsaturated fatty acid (such as monoester, diester, triester and the like produced from the unsaturated fatty acid and a compound having one or more hydroxyl groups per molecule) (preferably at least one selected from the group consisting of monoamide, monoester, diester and triester of the unsaturated fatty acid, particularly at least one selected from the group consisting of mono-(hydroxyl substituted C1-6 alkyl) monoamide, di-(hydroxyl substituted C1-6 alkyl) monoamide and triglyceride of the unsaturated fatty acid), and/or the unsaturated fatty acid has n carbon-carbon double bonds (n is an integer of 1-10, 1-8, 1-6, 1-4, 1-3 or 1-2).

9. The method according to any one of the preceding or subsequent aspects, wherein the derivative of the unsaturated fatty acid is a derivative produced from at least one unsaturated fatty acid selected from the group consisting of octadecenoic acid (e.g., 9-octadecenoic acid, particularly (Z)-9-octadecenoic acid) and octadecadienoic acid (e.g., 9,12-octadecadienoic acid, particularly (9Z,12Z)-9,12-octadecadienoic acid) and at least one member selected from the group consisting of glycerol, monoethanolamine and diethanolamine, preferably at least one selected from the group consisting of monoethanolmonoamide, diethanolmonoamide and triglyceride.

10. The method according to any one of the preceding or subsequent aspects, wherein the inorganic zinc compound is at least one selected from the group consisting of zinc oxide and inorganic zinc salts (preferably at least one selected from zinc oxide and zinc carbonate), and/or the benzothiazole-based sulfurization accelerator is at least one selected from the group consisting of mercaptobenzothiazole and mercaptobenzothiazole derivatives (preferably a compound represented by formula (A), more preferably at least one selected from 2-mercaptobenzothiazole, sodium 2-mercaptobenzothiazole, 6-amino-2-mercaptobenzothiazole and sodium 6-amino-2-mercaptobenzothiazole, still more preferably at least one selected from 2-mercaptobenzothiazole and 6-amino-2-mercaptobenzothiazole), (A)

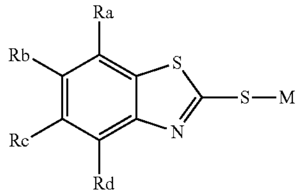

wherein in the formula (A), Ra, Rb, Rc and Rd, being the same or different from each other, are each independently selected from the group consisting of hydrogen, C1-4 alkyl, hydroxyl, amino and mercapto (preferably, Ra, Rc and Rd are hydrogen, Rb is selected from the group consisting of hydrogen, C1-4 alkyl, hydroxyl, amino and mercapto), M is selected from the group consisting of hydrogen, alkali metal (such as K or Na), ammonium ($NH_4$) and C1-4 alkyl, and/or the long-chain fatty acid is at least one selected from the group consisting of C10-22 (preferably C12-18) saturated or unsaturated fatty acids optionally substituted with one or more (such as 1, 2, 3, 4, 5 or 6) hydroxyl groups, preferably at least one selected from lauric acid, palmitic acid, oleic acid, stearic acid and ricinoleic acid, and/or the conditions of the sulfurization reaction include: a reaction temperature of 80-150° C. (preferably 100-130° C.) and a reaction time of 0.5-5 hr (preferably 1-3 hr).

11. A vegetable oil composition, comprising a vegetable oil and a sulfur-containing component, wherein the sulfur-containing component comprises the cyclic thioether compound as described in any one of the preceeding or subsequent aspects or a cyclic thioether compound produced by the method as described in any one of the preceeding or subsequent aspects, or comprising (preferably is) a product mixture produced by the method as described in any one of the preceeding or subsequent aspects.

12. The vegetable oil composition according to any one of the preceding or subsequent aspects, wherein the composition is a drilling fluid lubricant, and/or the cyclic thioether compound (calculated as

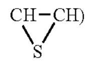

is present in an amount of 1-15 wt % (preferably 1.4-9.5 wt %), based on the total amount of the vegetable oil composition taken as 100 wt %, and/or its kinematic viscosity is typically 50-400 $mm^2/s$ (preferably 70-180 $mm^2/s$).

13. A drilling fluid composition, comprising a drilling fluid base slurry, a lubricant and optionally at least one treating agent, wherein the lubricant comprises or is the cyclic thioether compound as described in any one of the preceding or subsequent aspects, a cyclic thioether compound produced by the method as described in any one of the preceding or subsequent aspects, a product mixture produced by the method as described in any one of the preceding or subsequent aspects or the vegetable oil composition as described in any one of the preceding or subsequent aspects. 14. The drilling fluid composition as described in any one of the preceding or subsequent aspects, wherein the cyclic thioether compound (calculated as

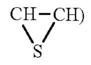

is present in an amount of 0.005-0.3 wt % (preferably 0.007-0.19 wt %), or the product mixture is present in an amount of 0.5-10.0 wt % (preferably 1.5-5.0 wt %), or the vegetable oil composition is present in an amount of 0.5-10.0 wt % (preferably 1.5-5.0 wt %), based on the total amount of the drilling fluid composition taken as 100 wt %.

15. A method for producing a drilling fluid composition, comprising the steps of:

producing a product mixture according to the method as described in any one of the preceeding or subsequent aspects, and mixing a drilling fluid base slurry and optionally at least one treating agent with the product mixture to obtain the drilling fluid composition.

Technical Effects

The active sulfurization system according to the present application has a relatively higher sulfurization activity, and allows a sulfurization of the vegetable oil under a lower temperature and in a shorter time than prior arts.

As compared with prior arts, by using the active sulfurization system of the present application, the odor emitted due to the oxidative decomposition of sulfur element during the sulfurization of vegetable oil at a high temperature for a long time can be greatly reduced because of the reduction of the sulfurization temperature and the shortening of the sulfurization time, so that compared with the sulfurized vegetable oil formed in the prior art, the sulfurized vegetable oil formed in the present application may not emit strong odor. On the other hand, the crosslinking of sulfurized vegetable oil at a high temperature can be prevented by sulfurizing at a low temperature for a short time, and the mass spectrum analysis of the sulfurized vegetable oil shows that the main structure of the sulfurized vegetable oil product is a cyclic thioetherified vegetable oil, and there is no bimolecular crosslinked structure of vegetable oil with a high molecular weight, so that the sulfurized vegetable oil of the present application has a higher flowability.

By using the active sulfurization system of the present application, a cyclic thioether structure can be introduced into vegetable oil. Without being bound by any theory, the inventors of the present application believe that the cyclic thioether structure can be chemically bonded with metal under extreme pressure conditions, so as to induce the vegetable oil/fat to form a firm hydrophobic lubricating film on a metallic friction surface, and therefore the vegetable oil sulfurized using the active sulfurization system has a strong lubricating capability.

DETAILED DESCRIPTION OF THE INVENTION

Figure 1:
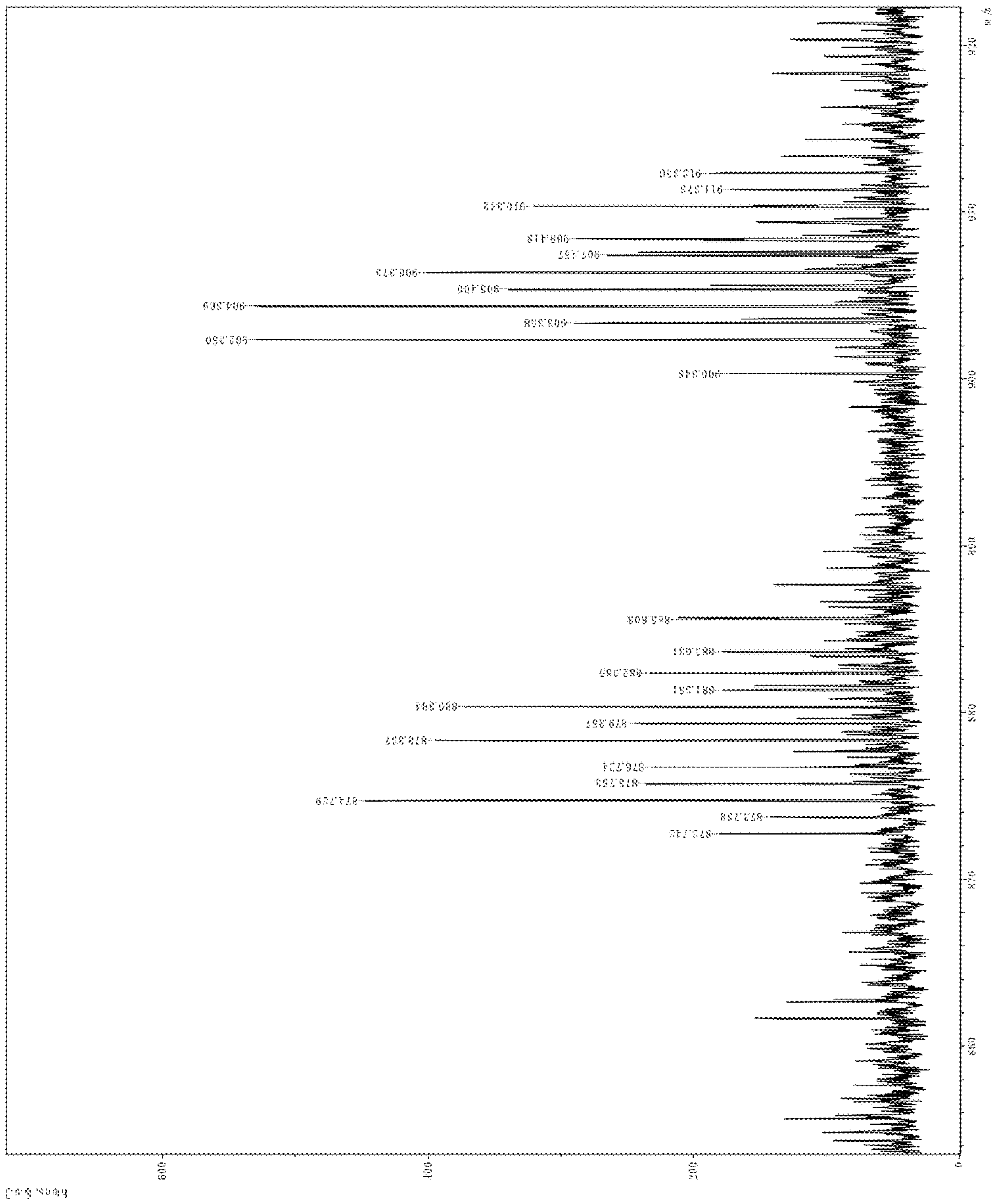
FIG. 1 is a diagram showing the mass spectrometry result of the reaction product obtained in Example 2.

The present application will be illustrated in detail hereinbelow with reference to embodiments thereof, but it should be noted that the scope of the present application is not limited by those embodiments, but is defined by the appended claims.

All publications, patent applications, patents, and other references cited herein are incorporated by reference in their entirety. Unless defined otherwise, all technical and scientific terms used herein have the same meaning as commonly understood by those skilled in the art. In case of conflict, the contents described herein, including definitions, should prevail.

When a material, method, component, apparatus, or device described herein is modified by an expression “known to those skilled in the art”, “commonly known in the art” or the like, it is to be understood that said material, method, component, apparatus, or device covers not only those conventionally used in the art at the time of filing the present application, but also those not commonly used at present but will become commonly known in the art to be suitable for a similar purpose.

In addition, all numerical ranges set forth herein are inclusive of their endpoints unless expressly stated otherwise. Further, when a numerical range, one or more preferred ranges, or a plurality of preferred upper limit values and preferred lower limit values are given for an amount, concentration, or other value or parameter, it is to be understood that all ranges formed by any pair of an upper limit of any range or any preferred value and a lower limit of any range or any other preferred value should be considered as explicitly disclosed herein, no matter whether such pairs of values are individually disclosed or not.

In the context of the present application, the kinematic viscosity is measured in accordance with the National Standard GB/T265-88. Specifically, a constant-temperature water bath is adjusted to 20° C., a sulfurized vegetable oil sample to be tested is placed into a glass capillary viscometer according to standard requirements, and the glass capillary viscometer is immersed into the constant-temperature water bath, installed in place, adjusted to be in a vertical state and kept at a constant temperature for 10 min; after the measuring instrument has reached a normal and stable state, the test is started and observation records are made, and the time for the sulfurized vegetable oil sample tested to flow through one calibrated glass capillary viscometer under the action of gravity is recorded using a stopwatch. The measurement was repeated 4 times, and the average value obtained from no less than 3 of the flow times measured is taken as the average flow time (sec/s) of the sample. The product of the measured flow time and the viscometer constant is recorded as the kinematic viscosity of the sulfurized vegetable oil sample tested, of which the unit is $mm^2/s$.

In the context of the present application, the expression “optionally substituted” means optionally substituted by one or more (such as 1 to 5, 1 to 4, 1 to 3, 1 to 2, or 1) substituents selected from the group consisting of hydroxyl, mercapto, amino, cyclic thioether group (i.e. a three-membered ring formed by one S atom with two adjacent carbon atoms), C1-10 linear or branched alkylamino, di-(C1-10 linear or branched alkyl)amino, C1-10 linear or branched alkyloxy and C1-10 linear or branched alkylthio, particularly optionally substituted with one or more (such as 1 to 5, 1 to 4, 1 to 3, 1 to 2, or 1) substituents selected from the group consisting of hydroxyl, mercapto, amino and cyclic thioether groups, more particularly substituted with one or more (such as 1 to 5, 1 to 4, 1 to 3, 1 to 2, or 1) substituents selected from hydroxyl and mercapto groups. Here, the C1-10 linear or branched alkyl is preferably a C1-4 linear or branched alkyl.

In the context of the present application, the expression “optionally interrupted” means that a hetero group selected from O, S and $NR_0$ is optionally inserted between any two adjacent carbon atoms (forming a carbon-carbon single bond) present in the group defined by the expression (typically a carbon chain, such as alkyl or alkylene group). Here, $R_0$ is selected from hydrogen and optionally substituted C1-10 linear or branched alkyl groups, preferably from hydrogen and optionally substituted C2-4 linear or branched alkyl groups. In addition, the interruption may occur one or more times, generally up to the total number n of carbon-carbon single bonds present in the group defined by the expression, or, for example, up to n/2, n/3 or n/4. Specific examples include, $CH_3—CH_2—CH_2—CH_2—$ can be interrupted once by O to obtain $CH_3—O—CH_2—CH_2—CH_2—$, $CH_3—CH_2—O—CH_2—CH_2—$ and $CH_3—CH_2—CH_2—O—CH_2—$, etc., can be interrupted twice by 0 to obtain $CH_3—O—CH_2—O—CH_2—CH_2—$, $CH_3—CH_2—O—CH_2—O—CH_2—$ and $CH_3—O—CH_2—CH_2—O—CH_2—$, etc., can be interrupted three times by O to obtain $CH_3—O—CH_2—O—CH_2—O—CH_2—$, can be interrupted once by S to obtain $CH_3—S—CH_2—CH_2—CH_2—$, $CH_3—CH_2—S—CH_2—CH_2—$ and $CH_3—CH_2—CH_2—S—CH_2—$, etc., can be interrupted once by $NCH_2CH_3$ to obtain $CH_3—(NCH_2CH_3)—CH_2—CH_2—CH_2—$, $CH_3—CH_2—(NCH_2CH_3)—CH_2—CH_2—$ and $CH_3—CH_2—CH_2—(NCH_2CH_3)—CH_2—$, etc., can be interrupted three times by $NCH_2CH_3$ to obtain $CH_3—(NCH_2CH_3)—CH_2—(NCH_2CH_3)—CH_2—(NCH_2CH_3)—CH_2—$, and can be interrupted once by $NCH_2CHOH$ to obtain $CH_3—(NCH_2CHOH)—CH_2—CH_2—CH_2—$, $CH_3—CH_2—(NCH_2CHOH)—CH_2—CH_2—$ and $CH_3—CH_2—CH_2—(NCH_2CHOH)—CH_2—$, etc. It should be noted that, in the case that said group, such as alkyl or alkylene group, has a relatively large number of carbon atoms, for example above C10 (up to C10000), the structure obtained by multiple interruptions by said hetero group actually corresponds to a polymer such as polyether, polythioether or polyimine, and the number of interruptions is equal to the value of polymerization degree of the polymer. For example, $—(CH_2—CH_2)_{1000}—$interrupted 1000 times by O gives $—(CH_2—CH_2\text{-}0)_{1000}—$or $—(O—CH_2—CH_2)_{1000}—$, both of which correspond to a polyether segment having a polymerization degree of 1000. In the present application, the polymerization degree of the polymer such as polyether, polythioether or polyimine may be generally 1 to 5000, preferably between 1 and 500. These polymers can be easily obtained by polymerization of ethylene oxide, propylene oxide, ethyleneimine, and the like.

In the context of the present application, unless specifically stated otherwise, the term "alkenyl" covers both mono-alkenyl (i.e., containing one carbon-carbon double bond) and poly-alkenyl (i.e., containing multiple carbon-carbon double bonds), while the term "poly-alkenyl" covers dienyl, trienyl, and tetraalkenyl groups, and the like, and more particularly covers conjugated dienyl groups and non-conjugated dienyl groups.

In the context of the present application, unless specifically stated otherwise, the term "alkynyl" covers both mono-alkynyl (i.e. containing one carbon-carbon triple bond) and poly-alkynyl (i.e. containing multiple carbon-carbon triple bonds), whereas the term "poly-alkynyl" covers di- and tri-alkynyl groups and the like.

In the context of the present application, unless specifically stated otherwise, the term "isomer" covers constitutional isomers and stereoisomers, the former including particularly carbon-chain isomers and positional isomers and the like, and the latter including particularly cis-trans isomers and optical isomers and the like.

In the context of the present application, unless specifically stated otherwise, all percentages, parts, ratios, etc. are expressed by weight and all pressures given are gauge pressures.

In the context of the present application, any two or more embodiments of the present application may be arbitrarily combined, and the resulting technical solution forms a part of the initial disclosure of the present application and falls within the scope of the present application.

According to an embodiment, the present application relates to a cyclic thioether compound. According to the present application, the cyclic thioether compound may be present as a simple compound or a mixture with other substances, and is not particularly limited. Furthermore, the cyclic thioether compound is particularly suitable for use as a drilling fluid lubricant.

According to an embodiment of the present application, the cyclic thioether compound has a structure represented by formula (I). Here, the structure represented by the formula (I) has an unbonded free end, which may be chemically bonded to any group, and there is no particular limitation.

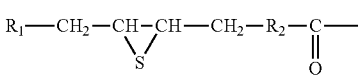
(I)

According to an embodiment of the present application, in the formula (I), $R_1$ is selected from optionally substituted C1-20, C2-10, C4-8 or C6-7 linear or branched hydrocarbyl groups, such as optionally substituted C1-20, C2-10, C4-8 or C6-7 linear or branched alkyl groups, optionally substituted C2-20, C2-10, C4-8 or C6-7 linear or branched alkenyl groups, or optionally substituted C2-20, C2-10, C4-8 or C6-7 linear or branched alkynyl groups.

According to an embodiment of the present application, in the formula (I), $R_2$ is selected from a single bond and optionally substituted C1-20, C2-10, C4-8 or C6-7 linear or branched hydrocarbylene groups, such as optionally substituted C1-20, C2-10, C4-8 or C6-7 linear or branched alkylene groups, optionally substituted C2-20, C2-10, C4-8 or C6-7 linear or branched alkenylene groups, or optionally substituted C2-20, C2-10, C4-8 or C6-7 linear or branched alkynylene groups.

According to an embodiment of the present application, in the formula (I), the sum of the numbers of carbon atoms of $R_1$ and $R_2$ is generally 3 or more, preferably 3 to 35, more preferably 5 to 25, or 11 to 13. Here, the sum of the numbers of carbon atoms of $R_1$ and $R_2$ does not include the number of carbon atoms of any substituent that may be present on $R_1$ and $R_2$.

According to an embodiment of the present application, the cyclic thioether compound has a structure represented by the following formula (I-1).

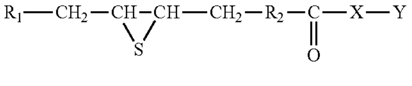
(I-1)

According to an embodiment of the present application, in the formula (I-1), X represents O or NR', wherein R' is selected from hydrogen and optionally substituted C1-10 linear or branched alkyl groups, preferably from hydrogen and optionally substituted C1-6 or C2-4 linear or branched alkyl groups.

According to an embodiment of the present application, in the formula (I-1), Y represents a monovalent end group, preferably selected from hydrogen, and optionally interrupted and optionally substituted C1-10000 linear or branched alkyl groups, more preferably from hydrogen, and optionally interrupted and optionally substituted C1-6 or C2-4 linear or branched alkyl groups. Alternatively, Y represents a polyether group having a polymerization degree of between 1 and 5000, preferably a polyether group having a polymerization degree of between 1 and 500.

According to the present application, all groups and values shown in the formula (I-1) that are not explicitly defined may directly apply the corresponding definitions provided hereinbefore for the formula (I).

According to an embodiment of the present application, the cyclic thioether compound has a structure represented by the following formula (I-2).

(I-2)

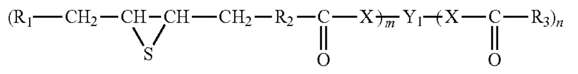

According to an embodiment of the present application, in the formula (I-2), each $R_3$, being the same or different from each other, is independently selected from optionally substituted C1-39, C9-23, C11-21 or C15-19 linear or branched hydrocarbyl group, such as optionally substituted C1-39, C9-23, C11-21 or C15-19 linear or branched alkyl groups, optionally substituted C3-39, C9-23, C11-21 or C15-19 linear or branched alkenyl groups, or optionally substituted C3-39, C9-23, C11-21 or C15-19 linear or branched alkynyl groups.

According to an embodiment of the present application, in the formula (I-2), m is an integer of 1 or more, preferably 1, 2, 3, 4, 5 or 6.

According to an embodiment of the present application, in the formula (I-2), n is an integer of 0 or more, preferably 0, 1, 2, 3, 4 or 5.

According to an embodiment of the present application, in the formula (I-2), m+n is an integer of 1 to 10, or 1 to 6, such as 1, 2, 3, 4, 5 or 6.

According to an embodiment of the present application, in the formula (I-2), each X, being the same or different from each other, is independently selected from 0 and NR', wherein R' is selected from hydrogen and optionally substituted C1-10 linear or branched alkyl groups, preferably from hydrogen and optionally substituted C1-6 or C2-4 linear or branched alkyl groups.

According to an embodiment of the present application, in the formula (I-2), $Y_1$ represents an optionally interrupted and optionally substituted m+n valent C2-10000 linear or branched alkyl group, preferably an optionally interrupted and optionally substituted m+n valent C2-6 or C2-4 linear or branched alkyl group, more preferably a 1,2,3-trivalent propyl group. Alternatively, $Y_1$ represents a m+n valent polyether group having a polymerization degree of 1-5000, preferably a m+n valent polyether group having a polymerization degree of 1-500, preferably m+n=2.

According to the present application, all groups and values shown in the formula (I-2) that are not explicitly defined may directly apply the corresponding definitions provided hereinbefore for the formula (I-1) or the formula (I).

According to an embodiment of the present application, the cyclic thioether compound is at least one selected from the group consisting of compounds represented by the following formulae and isomers thereof. Here, as the isomers, examples may, particularly, include various isomers distinguished from the compound disclosed in the position of the cyclic thioether group in the carbon chain, various isomers distinguished from the compound disclosed in the position of the carbon-carbon double bond in the carbon chain, and the like. The difference between those isomers and the compound disclosed has no substantial impact on the achievement of the technical effects of the present application, and thus those isomers also fall within the scope of the present application.

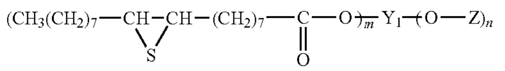

(I-3)

(I-3-1)

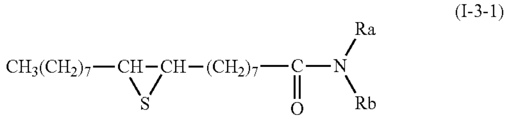

(I-3')

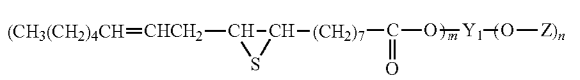

(I-3'-1)

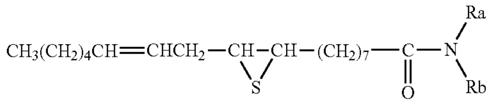

(I-3'')

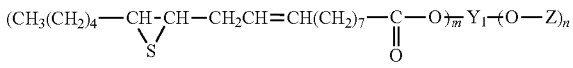

(I-3''-1)

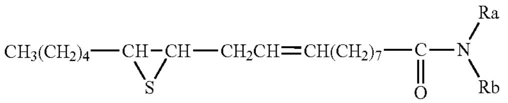

According to an embodiment of the present application, in those formulae, m is an integer of 1 or more, preferably 1, 2, 3, 4, 5 or 6, n is an integer of 0 or more, preferably 0, 1, 2, 3, 4 or 5, and m+n is an integer of 1 to 10, or 1 to 6, such as 1, 2, 3, 4, 5 or 6.

According to an embodiment of the present application, in those formulae, when m+n=3, $Y_1$ is a 1,2,3-trivalent propyl group. In this case, the cyclic thioether compound is a triglyceride containing a cyclic thioether group.

According to an embodiment of the present application, in these formulae, m=1 and n=0, $Y_1$ is an optionally interrupted and optionally substituted C2-10000 (preferably C2-6 or C2-4) linear or branched alkyl group or is a polyether group having a polymerization degree of between 1 and 5000, preferably a polyether group having a polymerization degree of between 1 and 500. In this case, the cyclic thioether compound is a monoester containing a cyclic thioether group.

According to an embodiment of the present application, in those formulae, each Z, being the same or different from each other, is independently selected from hydrogen, oleoyl group, linoleoyl group and stearoyl group. Here, the oleoyl group and linoleoyl group cover various isomers differentiated from each other in the position of the carbon-carbon double bond, and specific examples thereof include 9-oleoyl group, 10-oleoyl group, 11-oleoyl group, 9,12-linoleoyl group, 8, 11-linoleoyl group, 7, 10-linoleoyl group and the like. The numbers provided herein refer to the position of the double bond. According to an embodiment of the present application, in those formulae, Ra and Rb, being the same or different from each other, are each independently selected from hydrogen and hydroxyl substituted C1-10 linear or branched alkyl groups, preferably from hydrogen and hydroxyl substituted C1-6 or C2-4 linear or branched alkyl groups, more preferably from hydrogen and hydroxyethyl group. According to an embodiment of the present application, the present application also relates to a method for producing a cyclic thioether compound. This method can be used for producing the cyclic thioether compound or a material containing the cyclic thioether compound of the present application. According to an embodiment of the present application, the method for producing a cyclic thioether compound comprises the steps of: subjecting an unsaturated fatty acid starting material to a sulfurization reaction in the presence of sulfur, a benzothiazole-based sulfurization accelerator, an inorganic zinc compound and optionally a long-chain fatty acid, converting at least one carbon-carbon double bond of the unsaturated fatty acid starting material to a cyclic thioether moiety to obtain the cyclic thioether compound or a product mixture comprising the cyclic thioether compound. The cyclic thioether compound can be separated or purified from the product mixture after production, or can be used without separation or purification, preferably used without separation or purification.

According to an embodiment of the present application, in the method for producing a cyclic thioether compound, the at least one carbon-carbon double bond is non-conjugated double bond, that is, the at least one carbon-carbon double bond is not conjugated with other carbon-carbon double bond(s) (if any). Here, the number of the non-conjugated double bond(s) may be one or more than one, such as 1 to 10, 1 to 8, 1 to 6, 1 to 4, 1 to 3 or 1 to 2.

According to an embodiment of the present application, in the method for producing a cyclic thioether compound, the sulfur refers to elemental sulfur, and is generally used in the form of powder.

According to an embodiment of the present application, in the method for producing a cyclic thioether compound, the unsaturated fatty acid starting material is at least one selected from the group consisting of optionally substituted C8-40 (preferably C10-24, C16-20, or C18) unsaturated fatty acid (hereafter referred to as "unsaturated fatty acid" for short), derivatives of the unsaturated fatty acid (hereinafter, the unsaturated fatty acid and the derivative of the unsaturated fatty acid are collectively referred to as "unsaturated fatty acid compound"), and biomass materials comprising the unsaturated fatty acid compound. As the biomass material, vegetable oil may be particularly mentioned. Here, the unsaturated fatty acid starting material is preferably at least one selected from the group consisting of derivatives of the unsaturated fatty acid and vegetable oils comprising a derivative of the unsaturated fatty acid, particularly the vegetable oil.

According to an embodiment of the present application, in the method for producing a cyclic thioether compound, the vegetable oil is at least one selected from the group consisting of soybean oil, peanut oil, rapeseed oil, *camellia* oil, and corn oil. Here, the vegetable oil may be a fresh oil or a spent vegetable oil, such as drainage oil, and there is no particular limitation.

According to an embodiment of the present application, in the method for producing a cyclic thioether compound, the weight ratio of the sulfur:the benzothiazole-based sulfurization accelerator: the inorganic zinc compound: the unsaturated fatty acid compound (particularly the derivative of the unsaturated fatty acid): the long-chain fatty acid is generally 1-10:0.5-5:0.1-5: 75-98:0-10, preferably 1-6:0.7-7.8:0.3-1.2:79-95.6:2.4-6.

According to an embodiment of the present application, in the method for producing a cyclic thioether compound, the weight ratio of the sulfur: the benzothiazole-based sulfurization accelerator: the inorganic zinc compound:the biomass material (particularly the vegetable oil): the long-chain fatty acid is generally 1-10:0.5-5:0.1-5: 75-98:0-10, preferably 1-6:0.7-7.8:0.3-1.2:79-95.6:2.4-6. According to an embodiment of the present application, in the method for producing a cyclic thioether compound, the derivative of the unsaturated fatty acid is at least one selected from the group consisting of anhydride of the unsaturated fatty acid, amide of the unsaturated fatty acid, and ester of the unsaturated fatty acid. Examples of the amide of the unsaturated fatty acid include monoamides, diamides, and triamides formed from the unsaturated fatty acid and a compound having one or more primary and/or secondary amino groups per molecule, and more particularly include amides formed from the unsaturated fatty acid and monoethanolamine or diethanolamine. Examples of the ester of the unsaturated fatty acid include monoesters, diesters, and triesters formed from the unsaturated fatty acid and a compound having one or more hydroxyl groups per molecule, and more particularly include esters formed from the unsaturated fatty acid and ethylene glycol, polyethylene glycol, or glycerol. Preferably, the derivative of the unsaturated fatty acid is at least one selected from the group consisting of monoamide, monoester, diester and triester of the unsaturated fatty acid, particularly at least one selected from the group consisting of mono-(hydroxyl substituted C1-6 alkyl) monoamide, di-(hydroxyl substituted C1-6 alkyl) monoamide and triglyceride of the unsaturated fatty acid.

According to an embodiment of the present application, in the method for producing a cyclic thioether compound, the unsaturated fatty acid has n carbon-carbon double bonds, where n is an integer of 1 to 10, 1 to 8, 1 to 6, 1 to 4, 1 to 3, or 1 to 2. Here, the carbon-carbon double bond may be a conjugated double bond or a non-conjugated double bond, but at least one of them is a non-conjugated double bond as described hereinabove.

According to an embodiment of the present application, in the method for producing a cyclic thioether compound, the derivative of the unsaturated fatty acid is a derivative formed from at least one unsaturated fatty acid selected from the group consisting of octadecenoic acid and octadecadienoic acid and at least one selected from the group consisting of glycerol, monoethanolamine, and diethanolamine. Specific examples of the octadecenoic acid include 9-octadecenoic acid, and particularly (Z)-9-octadecenoic acid. Specific examples of the octadecadienoic acid include 9,12-octadecadienoic acid, and particularly (9Z,12Z)-9,12-octadecadienoic acid. Preferably, the derivative of the unsaturated fatty acid is at least one selected from the group consisting of monoethanol monoamides, diethanol monoamides, and triglyceride of the unsaturated fatty acid.

According to an embodiment of the present application, in the method for producing a cyclic thioether compound, the inorganic zinc compound is at least one selected from the group consisting of zinc oxide and inorganic zinc salts, and preferably at least one selected from the group consisting of zinc oxide and zinc carbonate.

According to an embodiment of the present application, in the method for producing a cyclic thioether ether compound, the benzothiazole-based sulfurization accelerator is at least one selected from the group consisting of mercaptobenzothiazole and mercaptobenzothiazole derivatives, preferably a compound represented by formula (A), more preferably at least one selected from the group consisting of 2-mercaptobenzothiazole, sodium 2-mercaptobenzothiazole, 6-amino-2-mercaptobenzothiazole and sodium 6-amino-2-mercaptobenzothiazole, and more preferably at least one selected from the group consisting of 2-mercaptobenzothiazole and 6-amino-2-mercaptobenzothiazole.

(A)

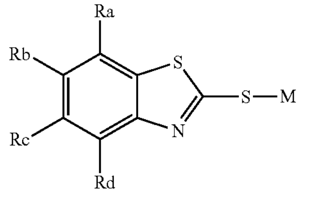

According to an embodiment of the present application, in the method for producing a cyclic thioether compound, in the formula (A), Ra, Rb, Rc and Rd, being the same or different from each other, are each independently selected from the group consisting of hydrogen, C1-4 alkyl, hydroxyl, amino and mercapto, preferably Ra, Rc and Rd are hydrogen, and Rb is selected from the group consisting of hydrogen, C1-4 alkyl, hydroxyl, amino and mercapto. Further, M is selected from hydrogen, alkali metal (such as K or Na), ammonium ($NH_4$) and C1-4 alkyl.

According to an embodiment of the present application, in the method for producing a cyclic thioether compound, the long-chain fatty acid is at least one selected from the group consisting of C10-22 (preferably C12-18) saturated or unsaturated fatty acids optionally substituted with one or more (such as 1, 2, 3, 4, 5, or 6) hydroxyl groups, preferably at least one selected from the group consisting of lauric acid, palmitic acid, oleic acid, stearic acid, and ricinoleic acid.

According to an embodiment of the present application, in the method for producing a cyclic thioether compound, the reaction temperature of the sulfurization reaction is 80-150° C., preferably 100-130° C. According to an embodiment of the present application, in the method for producing a cyclic thioether compound, the reaction time of the sulfurization reaction is 0.5-5 hours, preferably 1-3 hours. According to an embodiment of the present application, there is also provided a vegetable oil composition comprising a vegetable oil and a sulfur-containing component. Here, the sulfur-containing component comprises or is a cyclic thioether compound described in any of the embodiments provided hereinbefore or hereinafter. Alternatively, the sulfur-containing component comprises or is a cyclic thioether compound produced by the method described in any of the embodiments provided hereinbefore or hereinafter. Alternatively, the vegetable oil composition comprises the product mixture produced by the method described in any of the embodiments provided hereinbefore or hereinafter, preferably is the product mixture produced by the method described in any of the embodiments provided hereinbefore or hereinafter.

According to an embodiment of the present application, the vegetable oil composition is the product mixture produced by the method described in any of the embodiments provided hereinbefore or hereinafter. Specifically, according to this embodiment of the present application, the method for producing the vegetable oil composition comprises the steps of: subjecting the vegetable oil to a sulfurization reaction in the presence of sulfur, the benzothiazole-based sulfurization accelerator, the inorganic zinc compound and the optional long-chain fatty acid to obtain the vegetable oil composition (also referred to as "sulfurized vegetable oil"). Compared with the sulfurized vegetable oil described in the prior art, the sulfurized vegetable oil of the present application has an improved flowability, with its kinematic viscosity being generally 50-400 $mm^2/s$, and preferably 70-180 $mm^2/s$.

According to an embodiment of the present application, the vegetable oil composition is a drilling fluid lubricant. The drilling fluid lubricant can significantly improve the lubrication performance of the drilling fluid when used as a component of a drilling fluid composition.

According to an embodiment of the present application, the cyclic thioether compound (calculated as

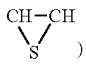
)

is present in an amount of 1-15 wt %, preferably 1.4-9.5 wt %, based on the total amount of the vegetable oil composition taken as 100 wt %.

According to an embodiment of the present application, there is also provided a drilling fluid composition comprising a drilling fluid base slurry, a lubricant, and optionally at least one treating agent. Here, the lubricant comprises or is a cyclic thioether compound described in any of the embodiments provided hereinbefore or hereinafter. Alternatively, the lubricant comprises or is a cyclic thioether compound or product mixture produced by the method described in any of the embodiments provided hereinbefore or hereinafter. Alternatively, the lubricant comprises or is a vegetable oil composition described in any of the embodiments provided hereinbefore or hereinafter.

According to an embodiment of the present application, the cyclic thioether compound (calculated as

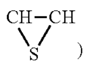
)

is present in an amount of 0.005-0.3 wt %, preferably 0.007-0.19 wt %, based on the total amount of the drilling fluid composition taken as 100 wt %.

According to an embodiment of the present application, the product mixture is present in an amount of 0.5-10.0 wt %, preferably 1.5-5.0 wt %, based on the total amount of the drilling fluid composition taken as 100 wt %.

According to an embodiment of the present application, the vegetable oil composition is present in an amount of 0.5-10.0 wt %, preferably 1.5-5.0 wt %, based on the total amount of the drilling fluid composition taken as 100 wt %.

According to an embodiment of the present application, there is also provided a method for producing a drilling fluid composition. The method can be used to produce a drilling fluid composition described in any of the embodiments provided hereinbefore or hereinafter.

According to an embodiment of the present application, the method for producing the drilling fluid composition comprises the steps of: producing the product mixture according to the method described in any of the embodiments provided hereinbefore or hereinafter, and then mixing a drilling fluid base slurry and optionally at least one treating agent with the product mixture to obtain the drilling fluid composition.

According to an embodiment of the present application, as examples of the drilling fluid base slurry and the treating agent, any one conventionally used in the art in drilling fluid compositions may be used without any particular limitation. Specific examples of the treating agent include at least one selected from the group consisting of thickener, flow pattern modifier, fluid loss additive, high-temperature stabilizer, blocking agent, inhibitor enhancer, and pH adjuster. In addition, the type and amount of the drilling fluid base slurry and the treating agent known in the art may be directly applied in the present application without any particular limitation.

EXAMPLES

The present application will be illustrated in further detail hereinbelow by way of examples and comparative examples, but the present application is not limited to the following examples.

Example 1

4 wt % of sulfur powder, 2 wt % of 2-mercaptobenzothiazole and 0.5 wt % of zinc oxide powder were added into a double-neck round bottom flask equipped with a reflux condenser pipe, heated to 130° C. in an oil bath equipped with a magnetic stirrer, stirred until the sulfur was melted and uniformly mixed to form an active sulfurization system. 93.5 wt % of soybean oil was added and mixed, reacted at 130° C. for 3 hours under heating, and cooled to obtain the targeted soybean oil sulfurized using the active sulfurization system.

From the appearance and microscopic image of the sulfurized soybean oil, no significant particulate insolubles were observed in the oil, indicating that the sulfur powder had reacted completely. Similar observations were also obtained in the following examples.

Example 2

4 wt % of sulfur powder, 2 wt % of 2-mercaptobenzothiazole, 0.5 wt % of zinc oxide powder and 3.5 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of soybean oil was added and mixed, reacted at 130° C. for 2 hours under heating, and cooled to obtain the targeted soybean oil sulfurized using the active sulfurization system, which had a kinematic viscosity of 152 $mm^2/s$.

The product of Example 2 was analyzed by mass spectrometry, see FIG. 1. From FIG. 1, characteristic peaks of linolin (compound a), triolein (compound b) and linolin with one ethylenic bond being cyclic thioetherified (i.e. compound c) can be found.

Compound a: HRMS (ESI+) m/z calcd for $C_{57}H_{99}O_6$ $[M+H]^+$ 879.744; found 879.357, having a structure represented by the following formula.

Comp. a

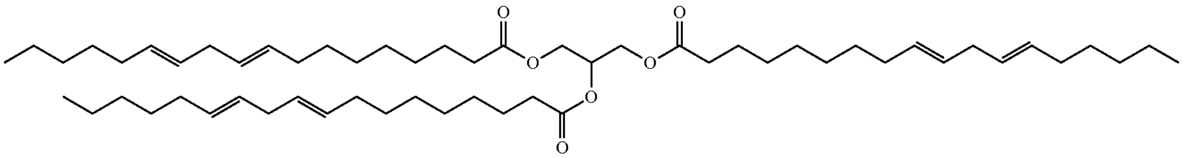

Compound b: HRMS (ESI+) m/z calcd for $C_{57}H_{105}O_6$ $[M+H]^+$ 885.791, having a structure represented by the following formula.

Comp. b

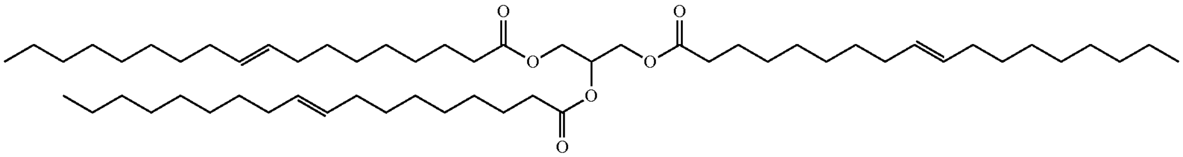

Compound c: HRMS (ESI+) m/z calcd for $C_{57}H_{99}O_6S$ $[M+H]^+$ 911.716; found 911.373, having a structure represented by the following formula.

Comp. c

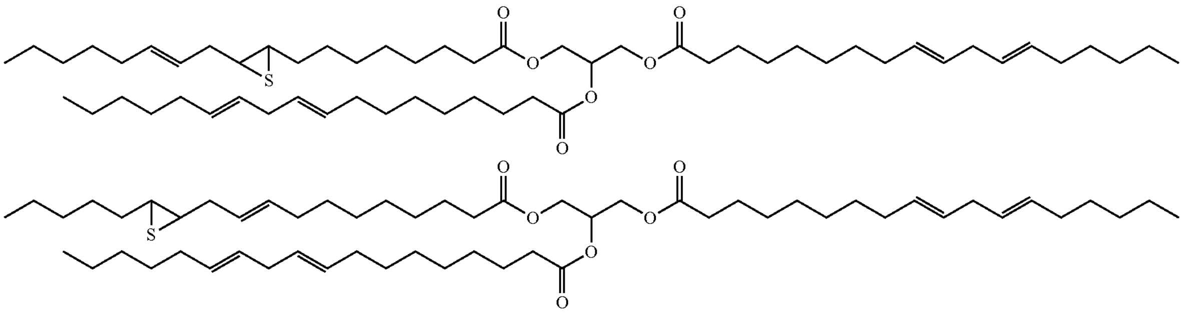

Example 3

4 wt % of sulfur powder, 2.3 wt % of 2-mercaptobenzothiazole, 0.7 wt % of zinc oxide powder and 3 wt % of lauric acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of rapeseed oil was added and mixed, reacted at 130° C. for 1 hour under heating, and cooled to obtain the targeted rapeseed oil sulfurized using the active sulfurization system.

Example 4

5 wt % of sulfur powder, 2.4 wt % of 2-mercaptobenzothiazole, 0.6 wt % of zinc oxide powder and 4 wt % of oleic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 88 wt % of peanut oil was added and mixed, reacted at 130° C. for 1 hour under heating, and cooled to obtain the targeted peanut oil sulfurized using the active sulfurization system.

Example 5

4 wt % of sulfur powder, 1.7 wt % of 2-mercaptobenzothiazole, 0.5 wt % of zinc oxide powder and 3.3 wt % of stearic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90.5 wt % of corn oil was added and mixed, reacted at 130° C. for 2 hours under heating, and cooled to obtain the targeted corn oil sulfurized using the active sulfurization system.

Example 6

6 wt % of sulfur powder, 2.3 wt % of 2-mercaptobenzothiazole, 0.7 wt % of zinc oxide powder and 5 wt % of ricinoleic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 86 wt % of *camellia* oil was added and mixed, reacted at 100° C. for 2 hours under heating, and cooled to obtain the targeted *camellia* oil sulfurized using the active sulfurization system.

Example 7

4 wt % of sulfur powder, 2.6 wt % of sodium 2-mercaptobenzothiazole, 0.5 wt % of zinc oxide powder and 2.4 wt % of lauric acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90.5 wt % of soybean oil was added and mixed, reacted at 130° C. for 2 hours under heating, and cooled to obtain the targeted soybean oil sulfurized using the active sulfurization system.

Example 8

4 wt % of sulfur powder, 2.6 wt % of 6-amino-2-mercaptobenzothiazole, 0.4 wt % of zinc oxide powder and 3 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of soybean oil was added and mixed, reacted at 130° C. for 2 hours under heating, and cooled to obtain the targeted soybean oil sulfurized using the active sulfurization system.

Example 9

4 wt % of sulfur powder, 1.8 wt % of 2-mercaptobenzothiazole, 1.2 wt % of zinc carbonate powder and 6 wt % of stearic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 87 wt % of soybean oil was added and mixed, reacted at 100° C. for 2 hours under heating, and cooled to obtain the targeted soybean oil sulfurized using the active sulfurization system.

Example 10

4 wt % of sulfur powder, 2 wt % of 2-mercaptobenzothiazole, 0.5 wt % of zinc oxide powder, 2 wt % of stearic acid and 1 wt % of lauric acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90.5 wt % of soybean oil was added and mixed, reacted at 130° C. for 2 hours under heating, and cooled to obtain the targeted soybean oil sulfurized using the active sulfurization system.

Example 11

4 wt % of sulfur powder, 2 wt % of 2-mercaptobenzothiazole, 0.5 wt % of zinc oxide powder and 3 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90.5 wt % of blend oil was added and mixed, reacted at 130° C. for 2 hours under heating, and cooled to obtain the targeted soybean oil sulfurized using the active sulfurization system.

Example 12

4 wt % of sulfur powder, 2 wt % of 2-mercaptobenzothiazole, 0.5 wt % of zinc oxide powder and 3.5 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of methyl oleate was added and mixed, reacted at 130° C. for 2 hours under heating, and cooled to obtain the targeted methyl oleate sulfurized using the active sulfurization system.

Figure 2:
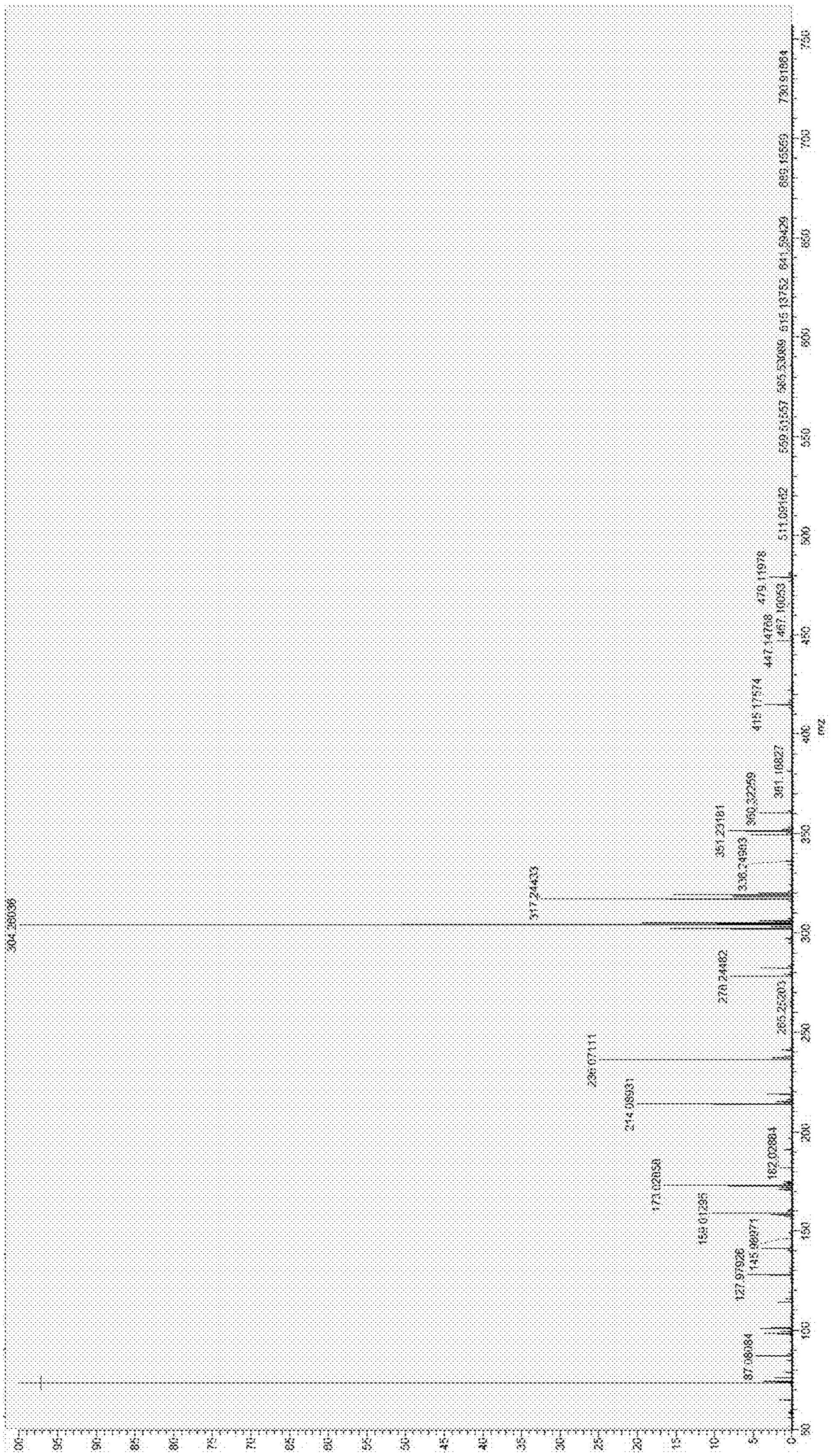
FIG. 2 is a diagram showing the mass spectrometry result of the reaction product ($R_f$=0.72) obtained in Example 12.

The product of Example 12 was subjected to column chromatography using a mixture of petroleum ether: ethyl acetate=20:1, and the material point with an $R_f$ of 0.72 was subjected to mass spectrometry, as shown in FIG. 2. From this FIG. 2, methyl linoleate (compound c) and cyclic thioetherified methyl linoleate (compound d) can be found.

Compound c: HRMS (ESI+) m/z calcd for $C_{19}H_{34}NaO_2$ [M+Na]+317.24510; found 317.24433, having a structure represented by the following formula.

Comp. c

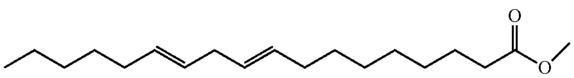

Compound d: HRMS (ESI+) m/z calcd for $C_{19}H_{36}NaO_2S$ $[M+Na]^+$351.23282; found 351.23181, having a structure represented by the following formula.

Comp. d

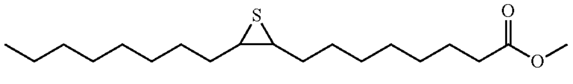

Example 13

4 wt % of sulfur powder, 2 wt % of 2-mercaptobenzothiazole, 0.5 wt % of zinc oxide powder and 3.5 wt % of palmitic acid were added into a double-neck round bottom flask with a reflux condenser pipe, heated in an oil bath equipped with a magnetic stirrer to 130° C., stirred until the sulfur was melted and uniformly mixed to form an active sulfurization system. 90 wt % of oleoyl diethanolamine was added and mixed, reacted at 130° C. for 2 hours under heating, and cooled to obtain the targeted oleoyl diethanolamine sulfurized using the active sulfurization system.

Example 14

80 wt % of soybean oil and 10 wt % of ethanolamine were added into a double-neck round bottom flask equipped with a reflux condenser pipe, and reacted at 150° C. for 2 hours to obtain an ammonolyzed soybean oil.

4 wt % of sulfur powder, 2 wt % of 2-mercaptobenzothiazole, 0.5 wt % of zinc oxide powder and 3.5 wt % of palmitic acid were heated in an oil bath equipped with a magnetic stirrer to 130° C., stirred until the sulfur was melted and uniformly mixed to form an active sulfurization system. The active sulfurization system was mixed with the prepared ammonolyzed soybean oil, reacted at 130° C. for 2 hours under heating, and cooled to obtain the targeted ammonolyzed soybean oil sulfurized using the active sulfurization system.

Example 15

4 wt % of sulfur powder, 2 wt % of 2-mercaptobenzothiazole, 0.5 wt % of zinc oxide powder and 3.5 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of ethylene glycol monooleate was added and mixed, reacted at 130° C. for 2 hours under heating, and cooled to obtain the targeted ethylene glycol monooleate sulfurized using the active sulfurization system.

Example 16

4 wt % of sulfur powder, 2 wt % of 2-mercaptobenzothiazole, 0.5 wt % of zinc oxide powder and 3.5 wt % of palmitic acid were added into a double-neck round bottom flask equipped with a reflux condenser pipe, heated in an oil bath equipped with a magnetic stirrer to 130° C., stirred until the sulfur was melted and uniformly mixed to form an active sulfurization system. 90 wt % of polyethylene glycol monooleate was added and mixed, reacted at 130° C. for 3 hours under heating, and cooled to obtain the targeted polyethylene glycol monooleate sulfurized using the active sulfurization system.

Comparative Example 1

4 wt % of sulfur powder was added into a double-neck round bottom flask equipped with a reflux condenser pipe, heated to 130° C. in an oil bath equipped with a magnetic stirrer, the sulfur powder was completely melted into a brown-yellow viscous liquid, 96 wt % of soybean oil was added and mixed, the resulting system was heated to 130° C., and reacted for 2 hours to obtain a sulfurized soybean oil.

Comparative Example 2

4 wt % of sulfur powder was added into a double-neck round bottom flask equipped with a reflux condenser pipe, heated in an oil bath equipped with a magnetic stirrer to 130° C., the sulfur powder was completely melted into a brown yellow viscous liquid, 96 wt % of soybean oil was added and mixed, the resulting system was heated to 150° C., and reacted for 5 hours to obtain a sulfurized soybean oil with a kinematic viscosity of 344 $mm^2/s$.

Comparative Example 3

4 wt % of sulfur powder and 2 wt % of 2-mercaptobenzothiazole were added into a double-neck round bottom flask equipped with a reflux condenser pipe, heated in an oil bath equipped with a magnetic stirrer to 130° C., reacted for 15 min, the resulting reaction system was a brown yellow viscous liquid, 94 wt % of soybean oil was added and mixed, reacted at 130° C. for 4 hours under heating, and cooled to obtain a sulfurized soybean oil.

Test Example

The method for determining the extreme pressure lubrication coefficient was as follows:

(1) Preparation of a base slurry: a base slurry was formulated at a ratio of distilled water:bentonite:anhydrous sodium carbonate=400 mL:20 g:0.7 g, mixed for 20 min using a high-speed mixer at a rotating speed of 11000 r/min, material adhered to the wall of the container and the stirrer was scraped off every 5 min, the resultant was sealed and maintained for 24 h at room temperature to obtain the base slurry.

(2) Determination of the extreme pressure lubrication coefficient: 2 g (i.e. 0.5%) of lubricant is added into the base slurry, the mixture was stirred using a high-speed stirrer at a rotating speed of 11000 r/min for 5 min, the extreme pressure lubrication coefficient of the mixed base slurry was determined, the reduction rate of the lubrication coefficient was calculated according to the following equation, and the lubrication coefficient of the base slurry was 0.684.

Calculation equation:

$$R = \frac{K_0 - K_1}{K_0} \times 100$$

In the equation:

R—reduction rate of lubrication coefficient, %;

$K_0$—lubrication coefficient of the base slurry;

$K_1$—lubrication coefficient of the base slurry after addition of the test sample.

TABLE 1

Comparison of the reaction results of different sulfurization systems

| Experiment No. | Temperature/time of sulfurization reaction | Sulfurization system | Lubrication coefficient | Reduction rate of lubrication coefficient | Properties of sulfurized oil |
|---|---|---|---|---|---|
| Comparative Example 1 | 130° C./2 h | Sulfur | 0.243 | 64.5% | Brownish-red oily liquid with precipitation of unreacted sulfur |
| Comparative Example 2 | 150° C./5 h | Sulfur | 0.182 | 73.4% | Brownish-black viscous liquid with pungent odor |
| Comparative Example 3 | 130° C./4 h | Sulfur/mercaptobenzothiazole | 0.168 | 75.4% | Brownish-red viscous liquid with slight pungent odor |
| Example 1 | 130° C./3 h | Sulfur/mercaptobenzothiazole/zinc oxide | 0.154 | 77.5% | Brown oily liquid with little white precipitate |
| Example 2 | 130° C./2 h | Sulfur/mercaptobenzothiazole/zinc oxide/palmitic acid | 0.132 | 80.7% | Brown oily liquid without pungent odor |

According to the present application, the reaction conditions and the lubrication performance of different sulfurized vegetable oils formed using different sulfurization systems are compared in Table 1, in which Comparative Example 1 and Comparative Example 2 show the sulfurization results obtained using sulfur as a sulfurizing agent for the vegetable oil under two different types of reaction conditions, i.e. low temperature and short time v.s. high temperature and long time. The results show that where the sulfurization was carried out at low temperature for a short time, a large amount of unreacted sulfur was separated out after the reaction system was cooled, and the sulfurized vegetable oil obtained had low sulfur content and poor lubricating effect because the sulfurization is incomplete. In contrast, although sulfur were fully consumed to form a sulfurized vegetable oil where the sulfurization was carried out at high temperature for a long time, the sulfurized vegetable oil obtained was black and thick and had pungent odor, which is adverse to field application.

On the other hand, in Comparative Example 3, mercaptobenzothiazole was added to the sulfur sulfurization system, and although the addition of mercaptobenzothiazole can reduce the sulfurization temperature and the reaction time, as well as the pungent odor of the sulfurized vegetable oil, to some extent, the improvement is not particularly evident.

As can be seen from the reaction conditions and the lubrication performance of Examples 1 and 2, the reaction conditions and the lubrication performance are greatly improved as compared to the comparative examples, and the sulfurization of the vegetable oil can be completed by reacting only at 130° C. for 2-3 h. Without being bound by any theory, the inventors of the present application believe that in Examples 1 and 2, zinc ions were incorporated into the structure of the sulfurization intermediate, i.e. bis(mercaptobenzothiazole)polythioether, formed by mercaptobenzothiazole and sulfur, thereby activating the sulfurization intermediate and greatly enhancing the activity of the sulfurizing agent. In addition, the vegetable oil sulfurization reaction time in Example 1 was prolonged as compared with that in Example 2, the sulfurized vegetable oil obtained comprised a little insoluble zinc oxide white precipitate, while the white precipitate in Example 2 disappeared, the reaction time was shortened, and the lubrication performance was further improved. The reason may be that, in Example 2, the large amount of fatty acid added continuously reacted with zinc oxide under heating to form zinc fatty acid salt, the zinc fatty acid salt could be dissolved in the reaction system, so that the concentration of zinc ions was increased, which further activated the active sulfurization system, and the large amount of fatty acid could act as a ligand to form a complex with zinc polythioether, which stabilized the active sulfurizing agent, so that a sulfurization system with higher activity was obtained. The fatty acid used in Example 1 is derived from vegetable oil, and the content and concentration of fatty acid in vegetable oil are low, so that the requirement of the reaction cannot be fully met.

The reaction conditions for the sulfurization of different vegetable oils using different sulfirization systems and the lubrication performance of the resulting different sulfurized vegetable oils are compared in Table 2. It can be seen that all of the active sulfurization systems formed by using different starting materials show excellent sulfurization performance, and the series of active sulfurization systems are used to sulfurize different types of vegetable oils, including a blend oil that is a mixture of a plurality of vegetable oils, and all of the sulfurized vegetable oil lubricants obtained show a reduction rate of lubrication coefficient of over 75% in a bentonite base slurry. The sulfurized vegetable oils obtained in Examples 4 and 6 show the best lubrication performance, and the fatty acids are unsaturated fatty acids that are oleic acid and ricinoleic acid, and can be sulfurized to form sulfurized oleic acid with a lubricating effect, so that the lubrication performance is further enhanced. On the other hand, the reaction temperature and reaction time of Examples 3, 4, 6 and 9 were reduced as compared to other examples because of the increased contents of zinc ions and fatty acids, which enhanced the activity of the active sulfurization system. This is also the reason why the reaction time was prolonged in Example 1, that is, without the addition of fatty acids, the contents of fatty acid ligands and zinc ions were reduced, and the activity of the sulfurization system was insufficient. In Example 12, methyl oleate was used as the substrate for sulfurization, and the lubrication performance was reduced relative to vegetable oil. This is probably because, being both fatty compounds, sulfurized methyl oleate has a shorter chain length and the lubricating film formed is less thick than sulfurized vegetable oils. In Examples 13, 14, 15 and 16, which are directed to the sulfurization of oleoyl diethanolamine, ammonolyzed vegetable oil, glycerol monooleate and polyethylene glycol monooleate, respectively, and the lubrication performance of the sulfurized product is superior to that of sulfurized vegetable oil, which is probably because the introduction of hydrophilic groups, i.e. the amino group, the hydroxyl group and the ether, improves the water dispersion capability of the system, thereby improving the lubrication performance.

TABLE 2

Comparison of reaction conditions and results of different sulfurization methods for producing sulfurized vegetable oils

| Experiment No. | Sulfurization system | Vegetable oil | Sulfurization temperature/ time | Lubrication Coefficient | decrease Rate of lubrication coefficient |
|---|---|---|---|---|---|
| Example 1 | Sulfur/mercaptobenzothiazole/ zinc oxide | Soybean oil | 130° C./3 h | 0.154 | 77.5% |
| Example 2 | Sulfur/mercaptobenzothiazole/ palmitic acid/zinc oxide | Soybean oil | 130° C./2 h | 0.132 | 80.7% |
| Example 3 | Sulfur/mercaptobenzothiazole/ lauric acid/zinc oxide | Rapeseed oil | 130° C./1 h | 0.156 | 77.2% |
| Example 4 | Sulfur/mercaptobenzothiazole/ oleic acid/zinc oxide | Peanut oil | 130° C./1 h | 0.092 | 86.5% |
| Example 5 | Sulfur/mercaptobenzothiazole/ stearic acid/zinc oxide | Corn oil | 130° C./2 h | 0.145 | 78.8% |
| Example 6 | Sulfur/sodium mercaptobenzothiazole/ ricinoleic acid/zinc oxide | Camellia seed oil | 100° C./2 h | 0.084 | 87.7% |
| Example 7 | Sulfur/sodium mercaptobenzothiazole/ lauric acid/zinc oxide | Soybean oil | 130° C./2 h | 0.148 | 78.3% |
| Example 8 | Sulfur/amino mercapto benzothiazole/palmitic acid/ zinc oxide | Soybean oil | 130° C./2 h | 0.125 | 81.7% |
| Example 9 | Sulfur/mercaptobenzothiazole/ stearic acid/zinc carbonate | Soybean oil | 100° C./2 h | 0.165 | 75.9% |
| Example 10 | Sulfur/mercaptobenzothiazole/ stearic acid/lauric acid/ zinc oxide | Soybean oil | 130° C./2 h | 0.152 | 77.8% |
| Example 11 | Sulfur/mercaptobenzothiazole/ palmitic acid/zinc oxide | Blend oil | 130° C./2 h | 0.127 | 81.4% |
| Example 12 | Sulfur/mercaptobenzothiazole/ palmitic acid/zinc oxide | Methyl oleate | 130° C./2 h | 0.163 | 76.2% |
| Example 13 | Sulfur/mercaptobenzothiazole/ palmitic acid/zinc oxide | oleoyl diethanolamine | 130° C./2 h | 0.109 | 84.1% |
| Example 14 | Sulfur/mercaptobenzothiazole/ palmitic acid/zinc oxide | Ammonolyzed soybean oil | 130° C./2 h | 0.091 | 86.7% |

TABLE 2-continued

Comparison of reaction conditions and results of different sulfurization methods for producing sulfurized vegetable oils

| Experiment No. | Sulfurization system | Vegetable oil | Sulfurization temperature/time | Lubrication Coefficient | decrease Rate of lubrication coefficient |
|---|---|---|---|---|---|
| Example 15 | Sulfur/mercaptobenzothiazole/palmitic acid/zinc oxide | Ethylene glycol monooleate | 130° C./2 h | 0.124 | 81.9% |
| Example 16 | Sulfur/mercaptobenzothiazole/palmitic acid/zinc oxide | Polyethylene glycol monooleate | 130° C./3 h | 0.071 | 89.6% |

The above examples of the present application are provided only for illustrative purpose, and have no limitation to the embodiments of the present application. Other variations and modifications will be apparent to those skilled in the art in light of the above description. It is not exhaustive here for all embodiments. Any obvious changes or modifications to the technical solution of the present application not departing from the spirit and scope of the invention described herein should be considered as falling within the scope of the present application.

The invention claimed is:

1. A cyclic thioether compound selected from the group consisting of compounds of formulae (I-3), (I-3'), and (I-3"):

(I-3)

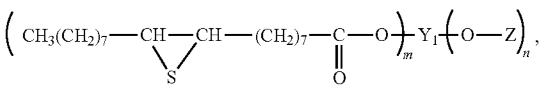, (I-3')

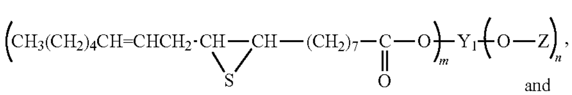, and (I-3")

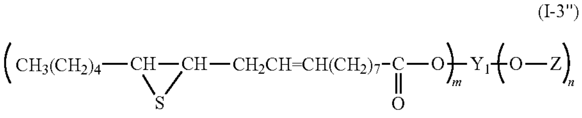

wherein:

m is 1, 2, or 3, n is 0, 1, or 2, m+n=3, $Y_1$ is a 1, 2, 3-trivalent propyl group, and each Z, being the same or different from each other, is independently oleoyl group or linoleoyl group.

2. A vegetable oil composition, comprising a vegetable oil and a sulfur-containing component, wherein the sulfur-containing component comprises the cyclic thioether compound according to claim 1.

3. The vegetable oil composition according to claim 2, wherein the composition is a drilling fluid lubricant, and/or the cyclic thioether compound, calculated as

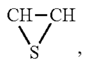, is present in an amount of 1-15 wt %, based on the total amount of the vegetable oil composition taken as 100 wt %, and/or kinematic viscosity of vegetable oil composition is 50-400 $mm^2/s$.

4. A drilling fluid composition, comprising a drilling fluid base slurry, a lubricant and optionally at least one treating agent, wherein the lubricant comprises or is the cyclic thioether compound according to claim 1.

5. The drilling fluid composition of claim 4, wherein the cyclic thioether compound, calculated as

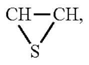

is present in an amount of is 0.005-0.3 wt %, or the vegetable oil composition is present in an amount of 0.5-10.0 wt %, based on the total amount of the drilling fluid composition taken as 100 wt %.

6. A drilling fluid composition, comprising a drilling fluid base slurry, and a lubricant, wherein the lubricant comprises or is the vegetable oil composition according to claim 2.

7. The cyclic thioether compound according to claim 1, wherein m is 1, and n is 2.

8. The vegetable oil composition according to claim 3, wherein the cyclic thioether compound, calculated as

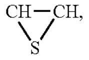

is present in an amount of 1.4-9.5 wt %, based on the total amount of the vegetable oil composition taken as 100 wt %, and/or, the kinematic viscosity of the vegetable oil composition is 70-180 $mm^2/s$.

* * * * *